United States Patent [19]

Kishimoto et al.

[11] Patent Number: 5,179,011
[45] Date of Patent: Jan. 12, 1993

[54] PROCESS FOR PRODUCING BIOTIN VITAMERS USING NOVEL MICROORGANISMS

[75] Inventors: Jiro Kishimoto; Shinichiro Haze; Ohji Ifuku, all of Yokohama, Japan

[73] Assignee: Shiseido Company Ltd., Tokyo, Japan

[21] Appl. No.: 672,913

[22] Filed: Mar. 21, 1991

[30] Foreign Application Priority Data

Mar. 27, 1990 [JP] Japan ................................. 2-75683

[51] Int. Cl.$^5$ ......................... C12P 17/18; C12R 1/19
[52] U.S. Cl. ............................... 435/119; 435/252.33; 435/320.1
[58] Field of Search ................. 435/119, 252.33, 320.1

[56] References Cited

U.S. PATENT DOCUMENTS 3,859,167  1/1975  Ogino et al. ........................ 435/119
4,563,426  1/1986  Yamada et al. .................... 435/119

FOREIGN PATENT DOCUMENTS 0316229  5/1989  European Pat. Off. .
155081   7/1987  Japan .

OTHER PUBLICATIONS

Newman et al, "Vol. Gen. Genet" (1981) 182 pp. 143–147, No. 1.
Japan Abs 61-149091 Hirano et al Nov. 20, 1986.
Japan Abs 61-202686 Ifuku et al Jan. 29, 1987.
Japan Abs 58-60996 Takakura et al Jun. 28, 1983.
Japan Abs 58-152495 Takakura et al Dec. 6, 1983.
Japan Abs 62-155081 Ifuku et al Jul. 10, 1987.
Japan Abs 02-27980 Komatsubara et al Apr. 11, 1990.
Japan Abs 56-160998 Yamada et al Mar. 19, 1982.

*Primary Examiner*—Herbert J. Lilling
*Attorney, Agent, or Firm*—Wegner, Cantor, Mueller & Player

[57] ABSTRACT

A mutant strain having a glucose consumption rate is at most ¼ that of wild type strains is provided. The mutant strain belongs to Escherichia, Bacillus, Pseudomonas, or Serratia; has a glucose consumption rate of at most one fourth that of the corresponding wild type strain, and the feedback repression by biotin is removed. Further, a process for producing biotins using this mutant strain is provided.

7 Claims, No Drawings

PROCESS FOR PRODUCING BIOTIN VITAMERS USING NOVEL MICROORGANISMS

FIELD OF THE INVENTION

The present invention relates to novel mutant strains having a glucose consumption rate which is at most ¼ that of wild type strains, particularly mutant strains which belongs to the genus Escherichia which are used for producing biotins. Further, the present invention relates to a process for producing biotin vitamers using these mutant strains.

DESCRIPTION OF THE RELATED ART

Various mutant strains have been produced in order to enhance the productivity of a specific useful substance. For example, in the general view of bacteria used for producing biotin, which is a vitamin important for animals, plants, and microorganisms, as the specific useful substance, those in which artificial mutated microorganisms such as the genus Bacillus, the genus Chromobacterium, the genus Pseudomonas, and the genus Arthrobacter are known. More specifically, in recent years, a strain which belongs to the genus Escherichia, which has a resistance to α-dehydrobiotin (for example, see Japanese Unexamined Patent Publication (Kokai) No. 61-149091), a strain which belongs to the genus Escherichia in which a feedback repression by biotin is removed (see, for example, Japanese Unexamined Patent Publication (Kokai) No. 61-202686), and a strain which belongs to the genus Escherichia, which has a reduced acetic acid productivity (see, for example, European Patent Publication No. 0316229) have been known as host microorganisms belong to the genus Escherichia for a host-vector system for application in a process of a recombination of a gene. As these microorganisms belong to genera other than the geuns Escherichia, those having a host for a specific recombinant plasmid which belongs to Bacillus, Pseudomonas, and Saccharomyces are known to be used (see, for example, Japanese Unexamined Patent Publication (Kokai) No. 64-44889). Note, the above-mentioned patent applications also disclose a process for producing biotins using a transformant having the recombinant plasmid corresponding to the host.

On the other hand, it is generally acknowledged that a mutation of an enzyme carrying phosphorylation of saccharide affects an assimilation of several saccharides, and models thereof have also been proposed [see, for example, "*Escherichia coli* and *Salmonella typhimurium*," F. C. Neidhardt, vol. 1, American Society For Microbiology: pp. 127-150, (1987)]. Nevertheless, there is no literature which describes the relationship therebetween them and the productivity of a specific substance.

In the case of biotin, which is an example of the useful substance produced by the aid of microorganisms, all of the mutant strains described above attainment a prescribed object, but there is still room for improvement. For example, in the case of European Patent Publication No. 0316229, which is one of the publications described above, an inexpensive and more efficient process compared with the prior one for producing biotins by the de novo synthesis by using a glucose as a substrate has been disclosed, the process using a genetic engineered, technically improved recombinant *Escherichia coli*, comprised of a mutant strain in which a feedback repression by biotin is removed as described above with a phenotype of decreasing acetic acid productivity imparted thereto as a host, and which contains a recombinant plasmid, in which biotin operons DNA obtained from *Escherichia coli* having a biotin productivity are inserted in the vector DNA.

There currently exists, however, needs to provide a mutant strain able to improve the productivity of a useful substance, particularly of biotin. Consequently, an object of the present invention is to provide a more efficient process for producing a specific useful substance by the use of microorganisms, especially for producing biotin by the use of microorganisms containing a biotin operon-inserted recombinant plasmid.

SUMMARY OF THE INVENTION

From a viewpoint different from the conventional view, i.e. from the viewpoint that, when grown with a usual fermentation medium which contains glucose as saccharides, although the wild type strain preferentially consumes glucose, a mutant strain having a decreased glucose assimilation capability preferentially consumes other carbon sources (such as amino acids). The glucose repression is relaxed, and thus the latter is expected to advantageously act on the productivity of the specific useful substance, and the inventors investigated the relation between such mutation of and the productivity of biotin, and as a result, some of these mutants containing the above-mentioned plasmid has been found to accumulate a considerable amount of biotin.

That is, the object described above can be solved by a mutant strain of a microorganism according to the present invention, which belongs to any one genera of Escherichia, Bacillus, and Serratia, characterized in that the maximum glucose consumption rate thereof is at most ¼ that of the corresponding wild strain.

In particular, the problems concerning the productivity of biotin can be solved by a process for producing biotins, which comprises cultivating the mutant strain described above, which contains a recombinant plasmid bearing a biotin operon originated from a microorganism which belongs to the genus Escherichia inserted in the vector DNA, in a nutrition medium, and then collecting biotin and/or desthiobiotin formed and accumulated in the medium.

DESCRIPTION OF THE PREFERRED EMBODIMENT

The mutant strains of the present invention should not be restricted and may be originated from any type of microorganisms which belong to any of the genus Escherichia, the genus Bacillus, and the genus Serratia, as long as they meet the object of the present invention. When used as a host-vector system, the mutant strains which belong to *Escherichia*, particularly originated from *Escherichia coli*, are preferable. Among them, the strains to be used in the production of biotins wherein feedback repression by biotin is removed (hereinafter referred sometimes to as "DR strains") are more preferable. Concrete examples of the strains used for the parent strains for the mutant strains include, but are not limited to, *Escherichia coli* strains DR-85 (FERM P-8096), DRK-332 (FERM BP-2113) and DRK-3323 (FERM BP-2116) (see Japanese Unexamined Patent Publications (Kokai) No. 61-202686, No. 62-155081, and European Patent Publication No. 0316299, described above).

All the numbers cited herein as "FERM" refer to the deposition numbers of the Fermentation Research Institute, Agency of Industrial Science and Technology in Japan.

From these parent strains, a mutant strain having a maximum value of the glucose consumption rate of at most one fourth that of the corresponding wild type strain, taking the following glucose consumption rate as an index, can be obtained with the known mutagenic treatment.

The "glucose consumption rate" used herein is the amount of glucose [(S) g/l] consumed by a unit amount of bacterial cells [(X) g/l] per unit time [(T) hr], and defined by the following equation. The term "corresponding wild type strain" used herein is a conception including mutant strains which mutation is different from the object of the present invention, which does not show any outstanding change in the glucose consumption capability.

$$\nu(\text{g glucose/g cell} \times \text{hr}) = 1/X \times dS/dT$$

In order to obtain the mutant strain described above, for example, microorganisms which have been mutagenically treated in a conventional manner, for example, mutagenically treated with a mutagenic reagent such as N-methyl-N'-nitro-N-nitrosoguanidine, are cultivated on a glucose assimilation-distinctive agar plate medium in accordance with the description of "Handbook for Products of Eiken Chemical Co., Ltd, 5th edition", and the mutant strains can be easily isolated as white colonies. This principle is based on the fact that, when the colonies are grown on the above-mentioned agar medium assimilate glucose contained in the medium, the pH value of the medium is lowered due to the organic acid and the like. Namely, the colonies become orange due to the dye "bromthymol blue" added to the medium; in contrast, the colonies formed by the mutant strain of the present invention obtained by the mutagenic treatment appears white because there is little change of the pH.

Concrete examples of the mutant strains thus obtained include the *Escherichia coli* DRG 024 strain, which was deposited in the Patent Microorganism Deposition Center in the Fermentation Research Institute, Agency of Industrial Science and Technology in Japan as described above, on Mar. 22, 1990, and imparted the deposition number of 11366, and then transferred the domestic authority to the International Depository Authority under the regulation of the Budapest Treaty as FERM BP-3309 on Mar. 14, 1991, as well as DRG 005 strain, DRG 014 strain, DRG 026 strain, and DRG 101 strain. It can be easily judged that such a mutant strain has gained the feature that the maximum glucose consumption rate thereof is at most one fourth that of the wild type strain, by cultivating the strain in a medium containing an adequate amount of glucose as the initial concentration, quantitatively determining the amount of the remaining glucose after a certain cultivation time by the use of an apparatus for measuring the concentration of glucose by utilizing an enzyme reaction, for example, Model 27 produced by YSI, and then comparing it with the wild type strains whose glucose assimilation capability can not be lowered. The preferred manner for determining the glucose consumption rate based on the glucose assimilation capability at the microorganism thus measured is described in Example 1 (2) later on.

The mutant strain obtained as described above (hereinafter referred sometimes to as "DG mutant strain") has an industrial applicability, for example, as can be advantageously used in the other aspect of the present invention. To be specific, according to the present invention, there is provided a mutant strain having a high producing- capability of biotin, in which the mutant strain described above is transformed with a recombinant plasmid bearing with a biotin operon originated from a microorganism which belong to the genus *Escherichia*, which is inserted in the vector DNA, and a process for producing biotins using the same.

The term "biotin vitamers" used herein means biotin itself, and its precursor desthiobiotin. As the recombinant plasmid which is transformed into the mutant strain of the present invention, any vectors may be used as long as they express the biotin productivity in the host-vector system. Preferably, pXBA312 and pKHN31 obtained from *Escherichi coli* strains DRK-3323 (pXBA312) (FERM BP-2117) and DRK-332 (pKHN31) (FERM BP-2114) provided by us, by a conventional method for isolating a plasmid can be mentioned.

The mutant strain according to the present invention having such a recombinant plasmid as described above can be obtained by transforming the recombinant plasmid obtained as described above into the DG mutant strain by the conventional method, such as a calcium chloride procedure described by Mandel M, et. al in "*J. Mol. Biol.*, 53, 109 (1970)", subsequently cultivating the resulting transformant on an agar medium in which the clones of the bacterial cells having the recombinant plasmid can be selectively grown, due to the phenotype of the vector therein, and fishing the colonies.

The DG mutant strains having the recombinant plasmid thus obtained include, for example, the *Escherichia coli* DRG 024 [pXBA312] strain, which was deposited in the Patent Microorganism Deposition Center in the Fermentation Research Institute, Agency of Industrial Science and Technology in Japan on Mar. 22, 1991 as described above, and imparted the deposition number of 11365, and then transferred the domestic authority to the International Depository Authority under the regulation of the Budapest Treaty as FERM BP-3308 on Mar. 14, 1991, as well as DRG 005 [pXBA312]strain, DRG 014 [pXBA312] strain, DRG 026 [pXBA312]-strain, and DRG 101 [pXBA312] strain.

By cultivating the microorganism thus obtained in a nutrient medium under adequate conditions usually used for cultivating a microorganism which belongs to the genus Escherichia, a considerable amount of the biotin can be accumulated in the culture. For example, as the nutrient medium, a known synthetic or natural medium containing carbon sources, nitrogen sources, and inorganic substances may be used. The carbon sources which can be used include carbohydrates such as glycerine, fructose, sucrose, maltose, mannose, starch, hydrolyzed starch liquor, molasses and the like. The amount used is preferably from approximately 0.5 to 5.0%. In the microorganism of the present invention, which has a reduced glucose assimilation capability, when a medium in which glucose is not strictly used as a single carbon source, for example, a natural medium containing yeast extract or casein hydrolysate described later on, is used, glucose also may be used as an available carbon source. In this case, the amount is desirably in the range of about 0.5 to 5.0%.

The nitrogen sources which may be used include ammonia, various inorganic or organic ammonium salts such as ammonium chloride, ammonium phosphate, ammonium sulfate, as well as natural organic nitrogen sources such as amino acids, meat extract, yeast extract, corn-steep liquor, casein hydrolysate, and defatted soybean or a digest thereof. In many cases, the natural organic nitrogen sources may be available not only as the nitrogen source but also as the carbon source.

As the inorganic substances, dipotassium hydrogenphosphate, potassium dihydrogenphosphate, magnesium sulfate, sodium chloride, ferrous sulfate, calcium chloride, zinc chloride, copper sulfate, manganese chloride, cobalt chloride, ammon molybdate, boric acid, and the like may be used.

The addition of alanine as described in Europe Patent Publication No. 0316229 is also available in the case of the DG strains of the present invention. The alanine used may be a D-compound, an L-compound, or a DL-compound, each of which brings about similar effects. The DL-compound is suitable in view of the cost. The concentration of alanine added to the medium is preferably 1–10 g/l, more preferably 3–7 g/l. Alanine may be added all at once at the beginning of the cultivation, or in portions during the cultivation.

In the case of the resulting microorganism to which a resistance to antibiotics is imparted, the contamination by other microorganisms may be prevented by adding the corresponding antibiotics to the medium. The cultivation is preferably carried out under aerobic conditions, for example, by shaking culture or aeration culture. The cultivation temperature is preferably 25°–37° C., and the pH value of the medium during the cultivation is preferably maintained to be substantially neutral. Concerning the production of biotin, the cultivation period is usually about 24–48 hours. When the cultivation continues for another 48 hours without adding any new nutrition, a significant accumulation of desthiobiotin can be obtained. After the completion of the cultivation, biotin or desthiobiotin can be collected from the culture broth by a general method for the extraction and purification from natural substances utilizing the properties of biotin or disthiobiotin. For example, biotin or desthiobiotin can be collected either by removing the bacterial cells from the cultivated substances, and treating the resultant culture broth with an activated carbon, and then eluting them, followed by purification by means of an ion-exchanging resin, or by directly treating the culture filtrate by means of an ion exchanging resin to be purified, followed by recrystallization from water or an alcohol.

According to the present invention, a novel microorganisms having a decreased glucose assimilation capability can be obtained, the microorganism being able to be used advantageously in the production of a specific useful substance. A microorganism obtained by using this microorganism as a host, and subjecting, for example, a recombinant plasmid in which biotin operon is inserted therein, to be incorporated in the host can advantageously be used in the production of the biotins.

EXAMPLE

The present invention will now be described in detail with reference to the working examples, which in no way limit the scope of the present invention.

EXAMPLE 1

(1) Preparation of DG mutant Strain from *Escherichia coli* in which Feedback Repression by Biotin is Removed

*Escherichia coli* DRK 3323 (FERM BP-2116) in which feedback repression has been removed was cultivated under shaking at 37° C. for 3 hours in an L-medium (10 g/l of peptone, 5 g/l of yeast extract, 1 g/l of glucose, 5 g/l of sodium chloride; adjusted to pH 7.2). Bacterial cells in a logarithmic growth phase were harvested, and washed, and then suspended in a TM buffer (0.61% of tris-base, 0.6% of maleic acid; adjusted to pH 6.0) containing 100 μg/ml of N-methyl-N'-nitro-N-nitrosoguanidine, and allowed to stand at 37° C. for 30 minutes for mutagenesis. After the bacterial cells were harvested and washed, the resuspended solution was applied on a normal sized Petri dish, which was layered on an agar plate medium (2 g/l of peptone, 10 g/l of glucose, 5 g/l of sodium chloride, 0.3 g/l of dipotassium hydrogenphosphate, 0.08 g/l of bromthymol blue; pH 7.0) obtained by changing the concentration of the agar in the medium for decomposing glucose according to the description of "Handbook for Products of Eiken Chemical Co., Ltd., 5th edition" into the concentration of the usual agar plate medium, such that about 200–800 colonies resulted. After cultivating at 37° C. for 48 hours, white or close to white colonies, which did not turn orange, were isolated by fishing to obtain DG mutant strains *Escherichia coli* in which the feedback repression by biotin was removed, i.e. DRG 024 strain (FERM BP-3309), DRG 005 strain, DRG 014 strain, DRG 026 strain, and DRG 101 strain.

As a pre-culture, the strains DRG 024, DRG 005, DRG 026, DRG 101, and DRK 3323 described above were inoculated with one application through a platinum loop from a maintenance agar plate culture to an L medium (10 g/l of peptone, 5 g/l of yeast extract, 1 g/l of glucose medium, 5 g/l of sodium chloride; adjusted to pH 7.0), and cultivated at 37° C. for 8–12 hours.

(2) Measurement of Glucose Consumption Rate

After 0.2 ml of this pre-culture was inoculated into a 500 ml volume Sakaguchi flask (produced by Iwaki Glass Co., Ltd.), a shaking culture was carried out at 37° C., the sample was taken every 2 hours, and the turbidity of the bacterial cells was measured to calculate the weight of dry bacterial cell (X) in terms of g/l. At the same time, an aliquot of the culture obtained was centrifuged, and 200 μl of the supernatant was injected into an apparatus for measuring the glucose concentration (produced from YSI; Model 27). The amount of remaining glucose was measured to determine the amount (S) of glucose consumed.

From these values, the glucose consumption rate (v) at each period of time was obtained according to a value number differential method using Gregory-Newton's formula:

$$v(g/glucose \times hr) = 1/X \times dS/dT$$

(See Engineering Mathematics, Vol. 1, Wily Ed. Brain Book Publisher, pp. 96).

The maximum values of the glucose consumption rate of each of the resulting DG mutant strains and the parent strain DRK 3323 (FERM BP-2116) are shown in Table 1.

| Medium-A | (g/l) |
| --- | --- |
| Disodium phosphate (12H$_2$O) | 17.6 |
| Potassium phosphate | 2.4 |
| Ammonium sulfate | 4.0 |
| Yeast extract | 10.0 |
| Peptone | 10.0 |

| Medium-A | (g/l) |
| --- | --- |
| Ferrous sulfate (7H₂O) | 0.1 |
| Calcium chloride (2H₂O) | 0.05 |
| Manganese chloride (4H₂O) | 0.05 |
| Magnesium sulfate (7H₂O) | 0.1 |
| Glucose | 5.0 |
| DL-Alanine | 5.0 |

TABLE 1

| Strain | Maximum value of Glucose Consumption Rate ($v$) |
| --- | --- |
| DRG 024 | 0.2 |
| DRG 005 | 0.05 |
| DRG 014 | 0.1 |
| DRG 026 | 0.5 |
| DRG 101 | 0.1 |
| DRK 3323 | 2.0 |

(3) Confirmation of Saccharide Assimilation Capability

DRG 005 strain, DRG 101 strain, and DRK 3323 were cultivated in the L-medium for 12 hours, and then washed twice with a PBS buffer. The aliquot amount of each cell was transferred to an M9 minimum synthetic medium containing a suitable saccharide or a metabolic intermediate listed in the table as a single carbon source in a concentration of 0.2% respectively. At 24 hours after the cultivation, it was determined whether or not the cells had grown. The results are shown in Table 2. In the DRG 005 strain and DRG 101 strain, it is clear that the assimilation capability of glucose and several other saccharides was lowered.

TABLE 2

| Strain (Saccharide added) | DRK 3323 | DRG 005 | DRG 101 |
| --- | --- | --- | --- |
| Glucose | + | − | − |
| Glycerol | + | − | + |
| Maltose | + | − | − |
| Fructose | + | − | − |
| Arabinose | + | + | + |
| Sodium Pyruvate | + | + | + |

EXAMPLE 2

Preparation of DG Mutant Strain containing Recombinant Plasmid

The *Escherichia coli* DRG 024 strain, DRG 005 strain, DRG 014 strain, DRG 026 strain, or DRG 101 strain was transformed with a recombinant plasmid pXBA 312 in which biotin operon was inserted in the vector DNA by the conventional method, for example, by a calcium method [Mol. Gen. Genet., Vol. 124, pp 1-10 (1973)], and then the colonies formed were isolated on an LB-solid medium plate containing 10 μg/ml of tetracycline to obtain DRG 024 [pXBA312] strain (FERM BP-3308), DRG 005 [pXBA312] strain, DRG 014 [pXBA312] strain, DRG 026 [pXBA312] strain, or DRG 101 [pXBA312] strain, respectively.

EXAMPLE 3

Preparation of Biotin

As a pre-culture, the DRG mutant strains containing the recombinant plasmid were inoculated with one application through a platinum loop from a maintenance agar plate culture to an L medium (10 g/l of peptone, 5 g/l of yeast extract, 1 g/l of glucose, 5 g/l of sodium chloride; adjusted to pH 7.0; in the case of the bacterial cells containing the recombinant plasmid, 20 μg/ml of tetracycline was further added thereto), and cultivated at 37° C. for 8-12 hours. 0.2 ml of this pre-culture was inoculated into a 500 ml volume Sakaguchi flask (produced by Iwaki Glass Co., Ltd.) containing 20 ml of the medium A described above, and then cultivated. After 96 hours, the sample was taken, and then the turbidity of the bacterial cells and the amounts of biotin and desthiobiotin accumulated were measured. The results are shown in Table 3.

For the quantitative analysis of biotin, the supernatant obtained after the centrifugation for removal of bacterial cells was diluted to an adequate degree, and a bioassay was carried out using *Lactobacillus plantarum* (ATCC 8014). For the quantitative analysis of desthiobiotin, the concentration of the sum of biotin and desthiobiotin was determined by colorimetry using avidin (Method in Enzymology, Vol. XVIII, pp. 49), and the amount of desthiobiotin was calculated by deducting the amount of biotin determined by the bioassay, as described above, from the sum.

TABLE 3

| Strain | Concentration of Cells (g/l) | Amount of Desthiobiotin Accumulated (mg/l) | Amount of Biotin Accumulated (mg/l) |
| --- | --- | --- | --- |
| DRG 024 [pXBA312] | 5 | 82 | 10 |
| DRG 005 [pXBA312] | 4 | 73 | 9 |
| DRG 014 [pXBA312] | 4 | 69 | 9 |
| DRG 026 [pXBA312] | 5 | 80 | 10 |
| DRG 101 [pXBA312] | 5 | 80 | 10 |
| DRK 3323 [pXBA312] (Control) | 4 | 13 | 9 |

We claim:

1. A process for producing biotin vitamers which comprises
   (a) cultivating in a nutrient medium a mutant strain of *E. coli* having
      (i) a glucose consumption rate of at most ¼ the rate of the corresponding wild strain,
      (ii) feedback repression by biotin removed, and operon originating from *E. coli* inserted in the vector DNA; and
   (b) collecting biotin and/or desthiobiotin formed and accumulated in the culture broth; wherein said process is characterized by the total production of desthiobiotin and biotin in an amount at least about 3.5 times greater than the corresponding parent strain of *E. coli*.

2. A process of claim 1, wherein said mutant strain is a strain selected from the group consisting of DRG 024, DRG 005, DRG 014, DRG 026, and DRG 101.

3. A process of claim 1, wherein said mutant strain is DRG 024.

4. A process of claim 1, wherein said mutant strain is DRG 005.

5. A process of claim 1, wherein said mutant strain is DRG 014.

6. A process of claim 1, wherein said mutant strain is DRG 026.

7. A process of claim 1, wherein said mutant strain is DRG 101.